(12) United States Patent
Schaaf (10) Patent No.: US 8,333,691 B2
(45) Date of Patent: Dec. 18, 2012

(54) ENDOSCOPE COMPRISING A FLEXIBLE PROBE (75) Inventor: Hansgeorg Schaaf, Reichertshausen (DE)

(73) Assignee: Polydiagnost GmbH, Pfaffenhofen (DE)

( * ) Notice: Subject to any disclaimer, the term of this patent is extended or adjusted under 35 U.S.C. 154(b) by 1455 days.

(21) Appl. No.: 10/587,981

(22) PCT Filed: Oct. 1, 2004

(86) PCT No.: PCT/EP2004/011050
§ 371 (c)(1),
(2), (4) Date: Aug. 3, 2006

(87) PCT Pub. No.: WO2005/074787
PCT Pub. Date: Aug. 18, 2005

(65) Prior Publication Data
US 2007/0129605 A1 Jun. 7, 2007

(30) Foreign Application Priority Data
Feb. 5, 2004 (DE) .......................... 10 2004 005 709

(51) Int. Cl.
*A61B 1/04* (2006.01)
*A61B 1/00* (2006.01)
*A61B 1/06* (2006.01)

(52) U.S. Cl. ........ 600/146; 600/114; 600/139; 600/147; 600/148; 600/160

(58) Field of Classification Search .................. 600/136, 600/137, 172, 175, 117, 154, 104, 106, 107, 600/114, 130, 139–142, 146–150, 160; 604/95.04, 604/523, 528
See application file for complete search history.

(56) References Cited

U.S. PATENT DOCUMENTS
4,487,489 A * 12/1984 Takamatsu ...................... 396/17
4,586,923 A * 5/1986 Gould et al. ............... 604/95.04
(Continued)

FOREIGN PATENT DOCUMENTS
DE        199 28 272 A1     1/2001
(Continued)

OTHER PUBLICATIONS
International Search Report dated Nov. 29, 2004 including English Translation of relevant portion (Six (6) pages).

*Primary Examiner* — Matthew J Kasztejna
*Assistant Examiner* — Ryan Henderson
(74) *Attorney, Agent, or Firm* — Crowell & Moring LLP (57) ABSTRACT An endoscope comprising a flexible catheter probe 1 having a plurality of lumens, a handle 12 provided at the proximal end of the probe, an optical system 6 provided in at least one optical system lumen of the catheter probe 1, at least one working lumen for a surgical instrument and a control element which is fixed to the distal end 20 of the probe or in the proximity thereof for bending the end of the probe and is guided movably in the axial direction at the probe, wherein the optical system 6 which projects beyond the proximal end of the catheter probe 1 is guided in a flexible tube which is elastically resilient in its longitudinal direction and exerts a prestressing on the optical system in the longitudinal direction thereof in a direction towards the translucently closed optical system lumen.

15 Claims, 4 Drawing Sheets

U.S. PATENT DOCUMENTS

| | | | |
|---|---|---|---|
| 4,762,120 A * | 8/1988 | Hussein | 600/136 |
| 4,779,612 A * | 10/1988 | Kishi | 600/141 |
| 4,919,112 A * | 4/1990 | Siegmund | 600/136 |
| 5,090,959 A * | 2/1992 | Samson et al. | 600/116 |
| 5,168,864 A * | 12/1992 | Shockey | 600/144 |
| 5,435,805 A | 7/1995 | Edwards et al. | |
| 5,569,161 A | 10/1996 | Ebling et al. | |
| 5,667,472 A * | 9/1997 | Finn et al. | 600/104 |
| 5,921,917 A * | 7/1999 | Barthel et al. | 600/120 |
| 6,083,152 A * | 7/2000 | Strong | 600/139 |
| 6,595,984 B1 * | 7/2003 | DeGuillebon | 606/1 |
| 2005/0272975 A1 * | 12/2005 | McWeeney et al. | 600/113 |

FOREIGN PATENT DOCUMENTS

| | | |
|---|---|---|
| DE | 201 18 886 U1 | 3/2002 |
| DE | 100 45 036 C1 | 7/2002 |
| DE | 103 51 013 A1 | 6/2005 |
| JP | 05-329216 | 12/1993 |
| JP | 2003-275173 | 9/2003 |
| WO | WO 9315648 A1 * | 8/1993 |

* cited by examiner

ENDOSCOPE COMPRISING A FLEXIBLE PROBE

BACKGROUND AND SUMMARY OF THE INVENTION

An endoscope of that kind is known from DE 100 45 036 C1. The known endoscope has a multi-lumen probe as well as a handle provided at the proximal end of the probe. An optical system extends in at least one of the probe lumens. There is also a working lumen for a surgical instrument. A control element for example in the form of a pulling wire or a pulling cable is connected to the distal end of the probe and is guided movably on the probe in the axial direction thereof. In that way a distal portion of the probe of a given length can be bent round and also rotated. That affords a therapeutic endoscope which can be easily used in surgical interventions.

U.S. Pat. No. 4,762,120 discloses an endoscope having a handle and a catheter arrangement in which the catheter arrangement is fixed rotatably and releasably to the handle. In the assembled condition the fibre optics provided in the catheter probe is aligned with the ocular optical means provided in the handle. For that purpose an optical means exit provided at the catheter arrangement is releasably connected to the handle. The catheter probe has further lumens whose exits at the proximal end are outside the handle. A control element for guiding the probe to the target location is not provided in that endoscope.

In the case of endoscopes with multi-lumen probes, maintenance and in particular decontamination are extremely difficult. That gives rise to high servicing costs and there are long interruption times between the respective uses in order to achieve reliable decontamination.

Therefore the object of the invention is to provide an endoscope having a controllable and flexible multi-lumen probe, in which simple maintenance is achieved and in particular difficulties which occur in decontamination are eliminated.

The invention provides that the proximal end portion of the optical system which projects beyond the proximal end of the catheter probe is guided in a flexible tube. The optical system which in particular is in the form of fibre optics preferably includes the observation optical system and the illumination optical system. The flexible tube is of an elastic nature in its longitudinal direction and can comprise for example silicone rubber. The tube is fixedly connected to the optical system at a fixing location which is removed from the proximal end of the catheter probe. Preferably the fixing location at which the tube is fixed to the optical system is disposed at the proximal end of the optical system. The elasticity of the tube provides that a prestressing is applied to the optical system in the longitudinal direction thereof so that the distal end of the optical system is pressed against a translucent cover provided at the distal end of the optical system lumen in the catheter probe as a closure element. In that arrangement the resiliently elastic tube is stressed between its distal tube end which is fixed releasably in the region of the proximal end of the probe and the fixing location to the optical system.

Advantageous developments of the invention are recited in the appendant claims.

The translucent sealing means or cover, for example in the form of a glass or plastic plate or disc, is fitted sealingly into the lumen material. The optical system lumen is hermetically closed off in relation to the target location, at the distal end. The translucent cover can also have optical properties, in particular imaging properties, and can be for example in the form of a lens. The translucent cover in the form of a plate or lens can be fitted in hermetically sealing relationship into the distal opening of the optical system lumen for example by adhesive, welding into the probe material which in particular comprises plastic material, or in the operation of shaping the probe by extrusion, injection moulding or the like. The optical system, in particular the illumination and observation optical system, is arranged displaceably in the optical system lumen and in the tube and is removable from the optical system lumen and the tube.

A connecting portion can be provided at the proximal end of the optical system, and an illumination device and/or an ocular can be connected to the connecting portion. The connecting portion has suitable adaptor devices for the connection of the illumination device and the ocular. As the illumination device it is also possible for an emergency illumination means which is possibly battery-operated to be connected to the connecting portion and thus to the illumination optical fibres of the optical system. The ocular is connected to the viewing fibre bundle of the optical system by way of the connecting portion.

The fixing location at which the proximal end of the tube is connected to the optical system can be provided at the connecting portion and is preferably in the form of a Luer lock connection. The optical system can be removed from the optical system lumen of the catheter probe and from the tube by virtue of the releasability of the connection of the optical system and the tube. Besides the prestressing effect on the optical system the tube also affords protection for the optical system between the proximal end of the catheter probe and the connecting portion.

By virtue of its elasticity the tube forms a length-compensating device which acts with a given prestressing force like a spring on the light guide/fibre bundle of the optical system. The distal end of the optical system is pressed against the translucent cover at the distal end of the optical system lumen and, when the distal portion of the probe is bent, the change in length is compensated by the resilient prestressing force. The optical system remains in contact against the cover with a certain pressing force. When the distal end of the probe moves back into the initial position of being aligned with the remaining portion of the probe, the optical system bundle is moved back into the initial position again by displacement in the optical system lumen in opposition to the resilient prestressing force.

Preferably the catheter probe is mounted rotatably to the handle. For that purpose the proximal end of the catheter probe can be supported in a rotary bearing on the handle. The rotary bearing preferably has a longitudinal bore which aligns with a control lumen of the catheter probe, in which the control element is arranged. The control element can thus be passed through the rotary bearing to a slider in or at the handle. The control element is fixedly connected to the slider. The control element can be displaced in the axial direction by the slider for bending the distal portion of the probe. The bent end of the probe can be additionally controlled by rotation of the catheter probe with respect to the handle. The rotary bearing permits a 360° rotation of the catheter probe with respect to the handle.

Fixing of the catheter probe to the rotary bearing is effected by means of a releasable fixing device, in particular a Luer lock connection. Fixing of the control element to the slider is also effected by means of a releasable fixing device, for example by means of a clamping screw.

Preferably the catheter probe is releasably connected to the rotary bearing on the handle only in the region of the guide wire lumen. The proximal exits for the other probe lumens are not connected to the handle. Those probe lumen exits can be connected to associated terminal devices independently of the handle and outside the handle. The optical system which is guided through the tube is connected outside the handle to the illumination system, for example an emergency illumination device, and to the ocular which can preferably be fixed to the handle, as already described hereinbefore. The observation optical system can also be connected in known manner by way of the ocular to a camera/monitor system or a suitable observation device.

In addition a flushing outlet at the proximal end of a flushing lumen of the probe can be connected to a flushing/suction removal system. In addition a working lumen or a plurality of working lumens for a surgical instrument or for a plurality of surgical instruments can be connected to actuating elements with which the respective surgical element is actuated. For that purpose the respective surgical element is guided removably in the associated working lumen.

The multi-lumen probe is preferably in the form of a disposable component. For that purpose the probe can be produced by injection moulding or extrusion or by another suitable shaping procedure and can comprise plastic material. Moreover an attachment portion of a strong material, for example plastic material, at which the lumen exits for the plurality of probe lumens and the guide exit which can be connected to the rotary bearing on the handle for the control element can be provided at the proximal end of the probe. The lumen exits and the guide exit can preferably have connecting elements for Luer locks, bayonet fixings or the like or can be in the form of coupling portions of such fixings and can also comprise the strong material of the proximal attachment portion. Preferably the proximal attachment portion can also be in the form of an injection moulding or extrusion which together with the flexible probe forms a disposable component.

Decontamination of the surgical instrument which can be removed from the working lumen can be effected in a simple fashion. The optical system which is removed from the optical system lumen is not contaminated during the surgical intervention as the distal end of the optical system volume is protected in relation to the target location by the translucent sealing means at the distal end and the surrounding probe material protects the optical system in terms of its lengthwise extent. As the catheter probe is preferably in the form of a disposable component a new probe which has not yet been used is connected to the handle, as described above, for a fresh use, in which case the optical system can be re-usably fitted into the optical system lumen.

Preferably the catheter probe can have a balloon to which a dilation medium, for example a gas or a liquid, for balloon expansion, can be fed by way of a balloon lumen in the catheter probe.

Furthermore the catheter probe can have a guide wire lumen through which a guide wire can be passed from the distal end of the probe to an exit opening disposed behind the balloon, in the catheter wall. Then, by means of the guide wire, the catheter probe can be guided to a target location in the body of the patient in particular with the portion of the probe which has the balloon or with the portion of the probe which can be flexurally deflected.

The control element is guided in a flexible support tube in the catheter probe. The support tube terminates at a spacing in front of the distal end of the catheter probe. That means that the flexibility and bendability of the portion of the probe which is to be bent is not adversely affected by the support tube. The spacing relative to the distal end corresponds approximately to the length of the distal portion of the probe, which is to be bent over by the control element.

Advantageously different catheter probes can be used with the handle, the optical system and the ocular, for different purposes of use in diagnostics and therapy. The handle, the optical system and the ocular form re-usable modular components which can be assembled to catheters of differing lengths, outside diameters and with differing numbers of lumens and with differing dimensions in respect of the diameters of the lumens, in particular working lumens, to form an endoscope which can be used in many different ways (multitasking endoscope). For example a widely varying range of instruments can also be directly incorporated in the working passage, being in particular mounted therein, so that an endoscope catheter with instrument forms a disposable system which does not give rise to any decontamination problems. The modular optical system which can be introduced affords a controllable and rotatable endoscopic instrument (visio instrument). In addition a balloon catheter can be embodied in the form of a disposable component with re-usable non-contamination optical system which can be removed from the balloon catheter.

BRIEF DESCRIPTION OF THE DRAWINGS

The invention is described in further detail hereinafter by means of an embodiment by way of example with reference to the Figures in which.

DETAILED DESCRIPTION OF THE DRAWINGS

Figure 1:
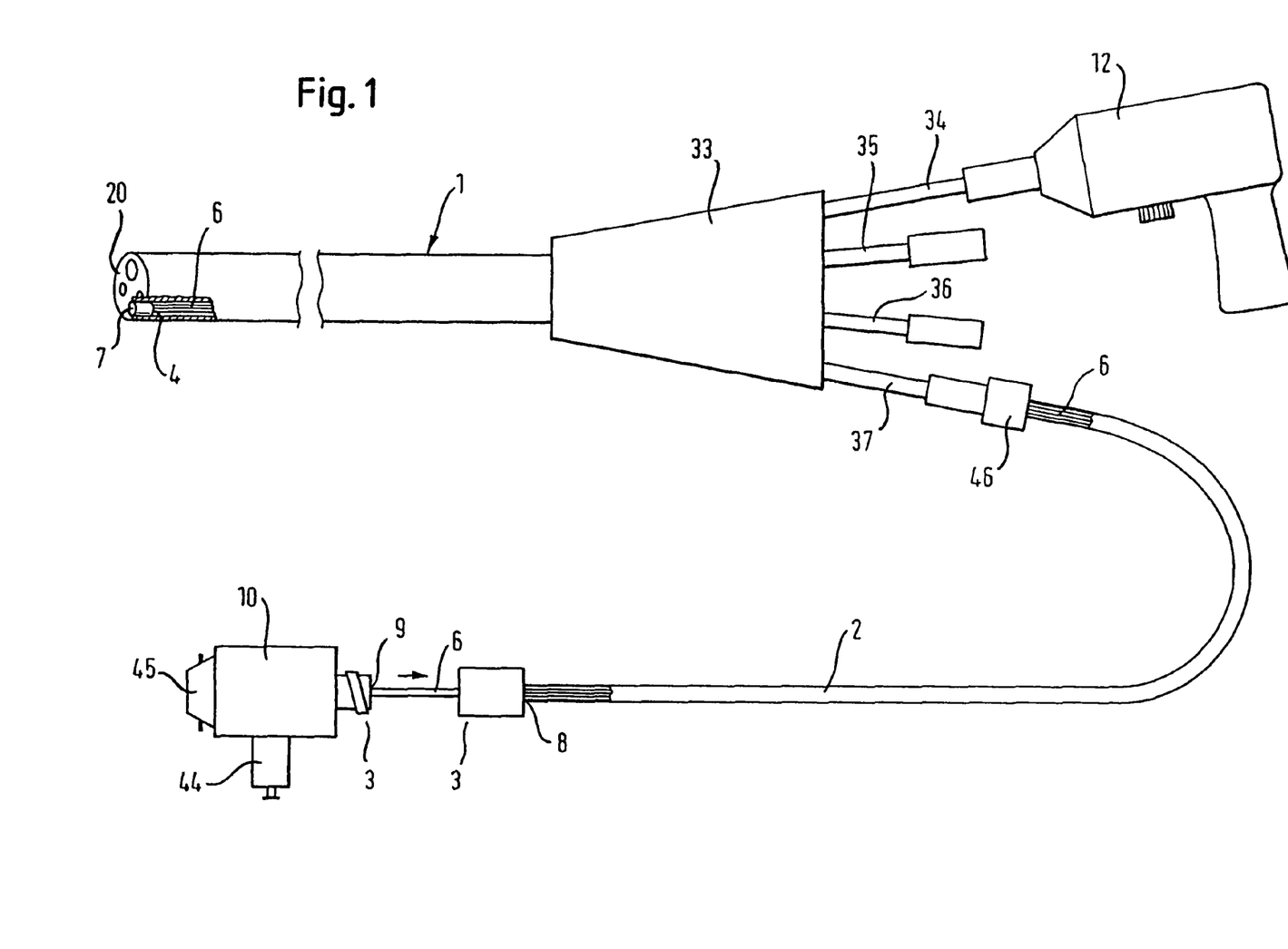
FIG. 1 is a diagrammatic view of an embodiment of the invention.
Figures 2, 3, 4:
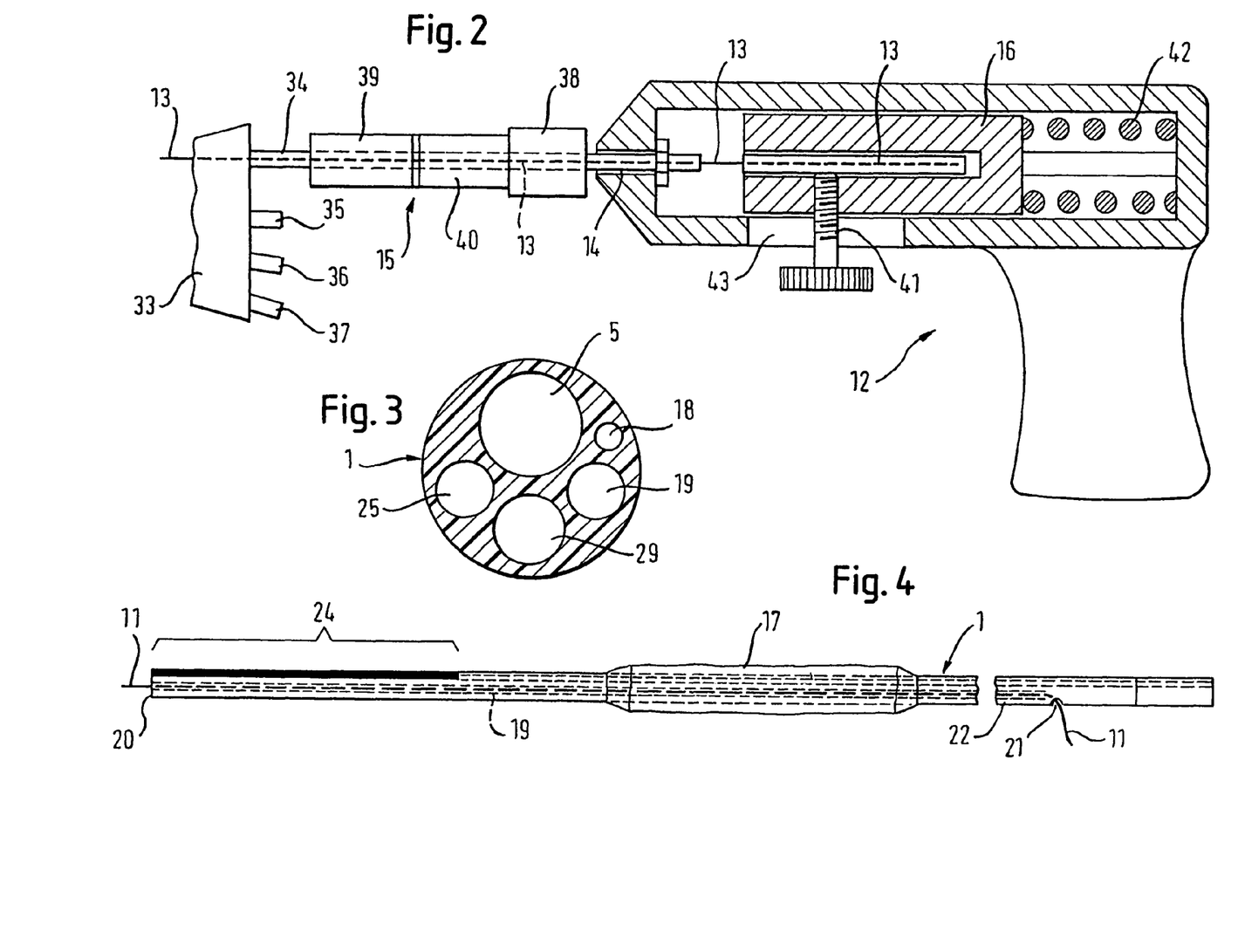
FIG. 2 shows an embodiment for rotatably fixing the catheter probe to the handle which can be used in the embodiment of FIG. 1.
FIG. 3 shows a section through a multi-lumen catheter probe which can be used in the embodiment of FIG. 1.
FIG. 4 shows a part of a probe which is in the form of a balloon catheter and which can be used in the embodiment of FIG. 1.

The embodiment of an endoscope as shown in FIG. 1 has a handle 12 and a catheter probe 1 to be releasably fixed thereto. The probe 1 is in the form of a multi-lumen probe (FIG. 3) and for example can have a working lumen or a plurality of working lumens 29 for surgical instruments and at least one optical system lumen 5 for an optical system 6. There can also be a balloon lumen 18 for dilation of a balloon 17 (FIG. 4). Separate optical system lumens can also be provided for the optical system 6 comprising the illumination optical system and the observation optical system. Likewise separate lumens can be provided in the probe 1 for flushing and suction removal.

Furthermore the catheter probe 1 includes a control element 13, for example in the form of a pulling wire or pulling cable. The elongate control element, as is known for example from DE 100 45 036 C1, is fixedly connected to a distal end 20 of the probe or is fixed in the proximity thereof and extends in the axial direction along the probe and is guided movably thereat. The distal end portion of the catheter probe 1 can be bent by the control element 13. As can be seen from FIGS. 5 and 6 the control element 13 extends through a support tube 23 which is arranged in a control lumen 25 of the catheter probe. The support tube 23 is also of a flexible nature. The support tube 23 terminates at a given spacing from the distal end 20 of the probe. That spacing corresponds approximately to the length of a portion 24 of the probe, which is to be bent over by the control element 13. The distal portion 24 of the probe which is to be bent over has a higher degree of flexibility than the portion of the catheter probe, in which the support tube 23 extends. In the region of its distal end the support tube 23 is fixed to the catheter probe 1, for example by means of an adhesive, in a fixing location 28. The fixing location 28 extends only over a slight axial distance of the support tube 23. With the rest of its length, the support tube 23 is arranged movably in the control lumen 25 of the catheter probe. The flexibility of the catheter probe is thus maintained over the major part of its length. In the region of the distal portion 24 of the probe which is to be bent over the catheter probe has a higher level of flexibility and bendability than in the remaining part of the probe in which the support tube 23 extends.

Figure 5:
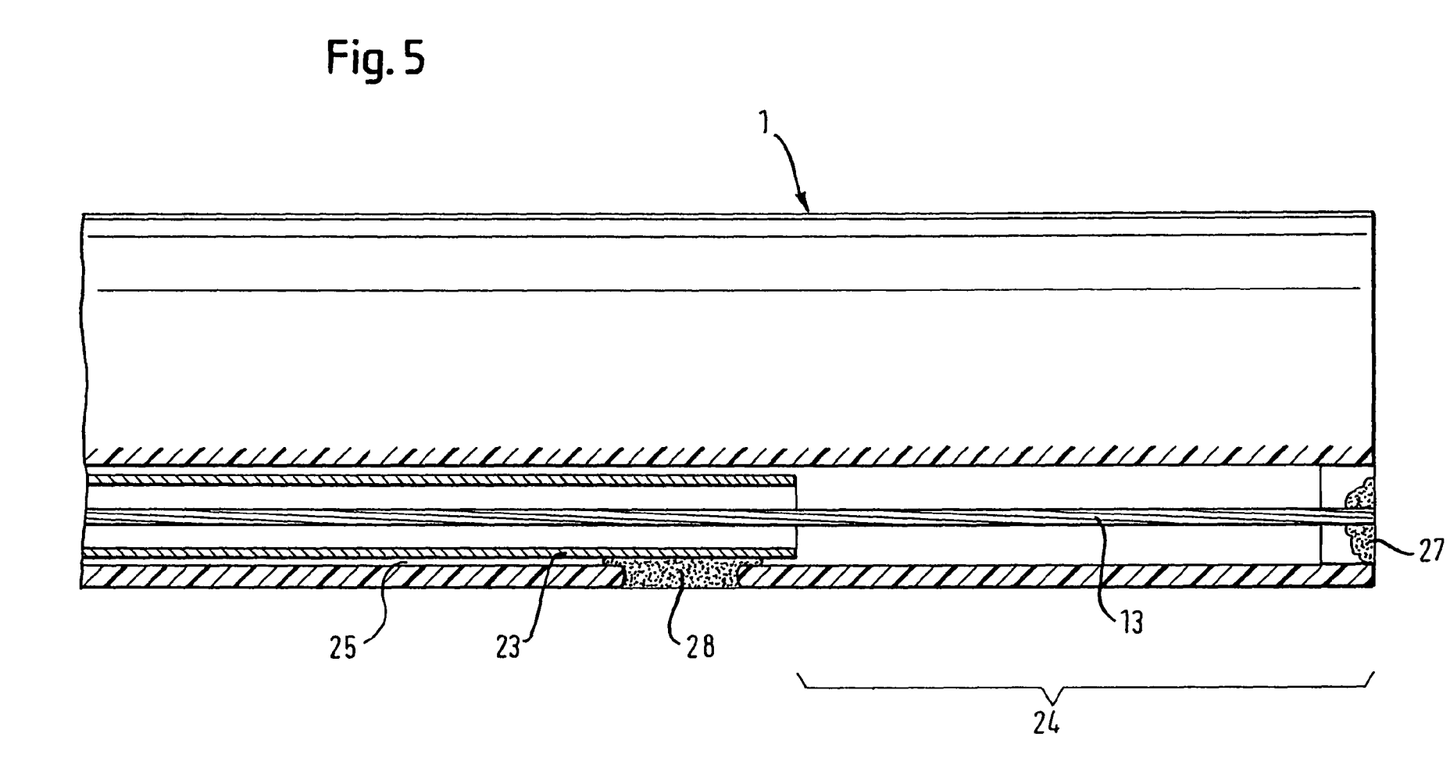
FIG. 5 shows an embodiment of a bendable distal portion of a catheter probe which can be used in the invention.
Figure 6:
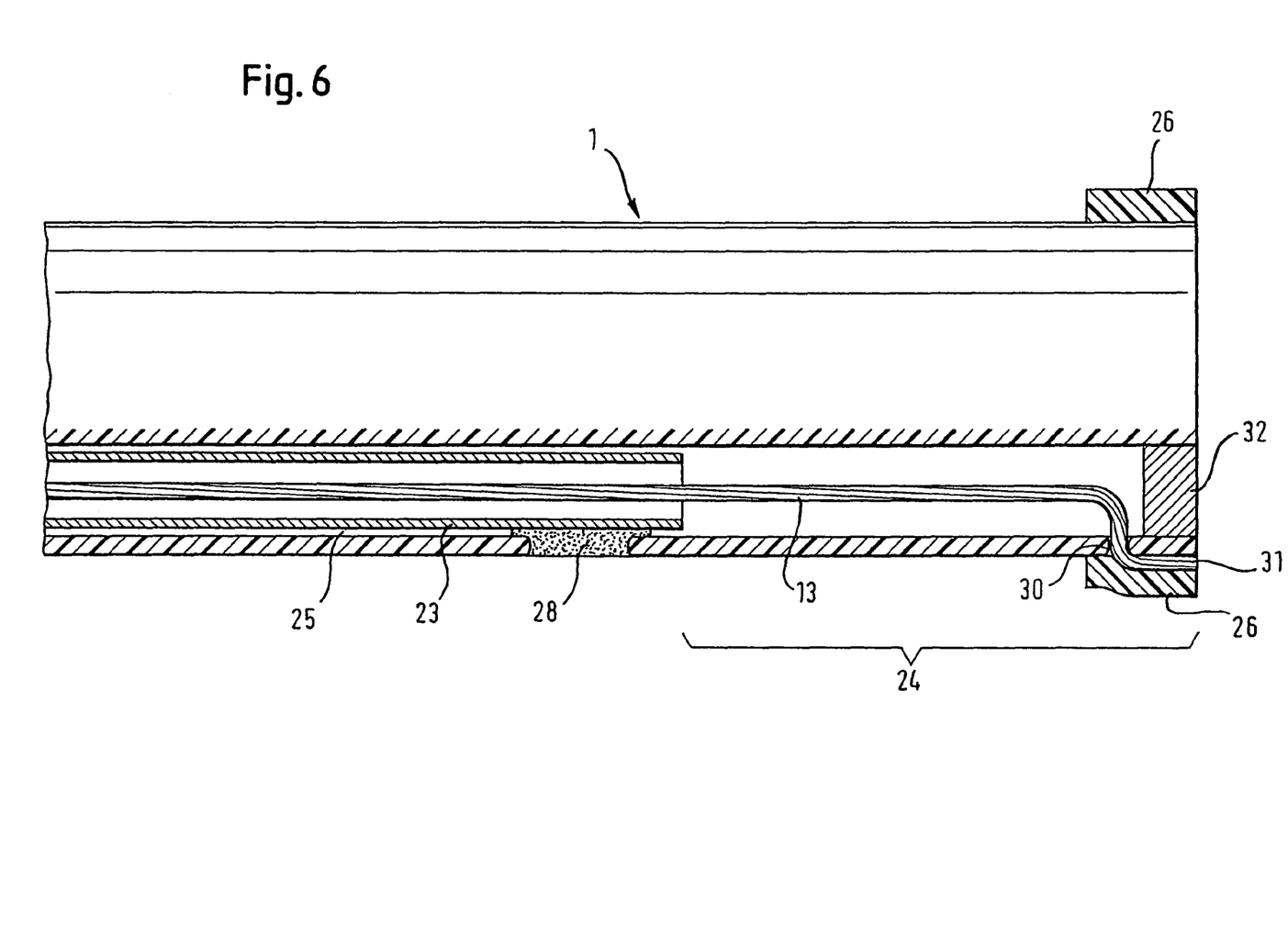
FIG. 6 shows a further embodiment of a bendable distal portion of a catheter probe which can be used in the invention.

The control element 13 which is preferably in the form of a pulling wire is fixed to the distal end 20 of the probe. In the embodiment of FIG. 5 fixing is effected by an adhesive 27. In the embodiment of FIG. 6 fixing is effected by a shrink tube 26. The end 31 of the pulling wire 13 which is guided from the inside through an opening 30 in the wall of the probe 1 is pressed against the outside of the distal end 20 of the probe by the shrink tube 26. The distal end of the control lumen 25 extending through the probe 1 is closed by a closure element 32. The distal portion 24 of the probe which is bendable by the control element 13 can also be of the configuration as is known from DE 201 18 886 U or DE 199 28 272 A1.

The catheter probe 1 comprises a bendable material, in particular biocompatible plastic material. It is preferably in the form of a disposable component which after a surgical use is released from the handle 12 and disposed of. In a further surgical intervention, a new catheter probe is fixed to the handle 12, having been kept in readiness in a sterile condition as a disposable component.

At the proximal end the catheter probe 1 has a probe attachment portion 33 comprising a rigid strong material. That material can also be a plastic material. Disposed on the probe attachment portion 33 are proximal lumen exits 34, 35, 36 and 37. The control element 13 is guided through the lumen exit 34. The lumen exit 35 is for example associated with the balloon lumen 18, the lumen exit 36 is associated for example with the working lumen 29 and the lumen exit 37 is associated for example with the optical system lumen 5. The exits are equipped in known manner with coupling elements, for example for a bayonet fixing, a Luer lock or with similar coupling and connecting portions.

The catheter probe 1 is connected non-rotatably by way of the rigid tubular lumen exit 34 for the control element 13 to a rotary bearing 14 on the handle 12, in particular on the handle housing (see FIG. 2). In the illustrated embodiment, at its front end the handle 12 has the rotary bearing 14 which can be connected with a releasable fixing device 15 to the lumen exit 34 provided on the probe attachment portion 33. The releasable fixing device 15 can be in the form of a bayonet fixing or Luer lock or the like. The releasable fixing device 15 provides a non-rotatable connection between the rotary bearing 14 on the handle 12 and the catheter probe 1. In that way rotary movements of a rotary portion 38, which is actuated for example by hand, of the rotary bearing 14 can be transmitted to the catheter probe 1 and in particular to the distal portion 24 of the probe, with the distal end 20 of the probe possibly being in the bent condition. The shaping for example of the probe attachment portion 33 or a marking on the catheter probe 1 or on the probe attachment portion 33 provides that it is possible to recognise the angular position of the catheter probe, in particular the position of the distal end 20 of the probe and the rotary angular position of the optical system 6 about the probe axis. In that case the catheter probe 1 can be rotated at an angle of 360° with respect to the handle 12. The releasable fixing device 15 has a coupling element 40 which is fixed to the rotary portion 38 and a coupling element 39 fixed to the lumen exit 34. This can involve coupling elements 39, 40 of a bayonet fixing or Luer lock or another releasable connecting device. The releasable fixing device 15 provided in that fashion has an axial bore which extends therethrough and which also passes through the rotary bearing 14. The control element 13 extends through that axially extending bore.

The proximal end of the control element 13 which is guided through the fixing device 15 and the rotary bearing 14 is connected fixedly to a slider 16 which is supported displaceably in the axial direction, by means of a releasable fixing means 41, for example in the form of a clamping screw.

The slider 16 is guided movably in the axial direction in the housing of the handle 12 against a prestressing force, for example of a prestressing spring 42. In this case the prestressing force acts in the direction towards the front (distal) end of the handle 12. In the foremost position of the slider the distal end 20 of the probe is not bent over with respect to the remaining region of the probe. When the slider 16 is displaced against the prestressing force of the spring 42 in the direction of the rearward (proximal) end of the handle 12, that movement is transmitted by way of the control element 13 to the distal end 20 of the probe and the distal end of the probe is bent over in dependence on the length of the displacement movement. Actuation of the slider 16 can be effected for example by means of an actuating element connected to the fixing means 41. For example the head of the clamping screw can be in the form of an actuating element. It is however also possible to provide an additional actuating element. For that purpose the actuating element can project through a slot 43 extending in the axial direction of the handle 12 in the housing of the handle, as is shown in FIG. 2 for the clamping screw which acts as a releasable fixing means 41. The slot 43 can form abutments at its two ends for limiting the movement of the slider 16 and the axial control movement of the control element 13.

To produce the axial slider movement it is also possible to provide a crank drive with which a pivotal or rotary movement produced at the outside of the handle is converted into the axial, linearly extending movement of the slider. A handle with a crank drive of that kind is described in DE 103 51 013 A1 (PCT/EP03/12897) and can be used in the embodiment of FIG. 1.

In addition an ocular holder (not shown in greater detail) can be arranged preferably pivotably on the handle 12, in particular at the rear (proximal) end.

As FIG. 1 shows the catheter probe 1 is connected to the handle 12 by means of the releasable fixing device 15 only by way of the proximal probe exit 34 for the control element 13. The other lumen exits 35, 36 and 37 are independent of the handle 12 and can be connected directly by way of suitable connecting apparatus to associated terminal devices. For example the proximal lumen exit 35 for the balloon lumen 18 can be connected by a suitable connecting portion to a dilation device (not shown in greater detail) which provides a liquid or gaseous dilation medium. In addition a surgical instrument, for example a borer with a flexible shaft, as is known for example from DE 101 078 156 A1, or an instrument for the removal of a foreign body and for reducing the size of a foreign body, in particular for use in mechanical lithotripsy, can be removably inserted into the working lumen 29 through the proximal lumen exit 36.

In addition a flushing or suction device can be connected to the working lumen 19 by way of the lumen exit 36.

The optical system 6 which includes an illumination and an observation optical system can be inserted into the optical system lumen 5 of the catheter probe 1 through the lumen exit 37. It is also possible to provide separate optical system lumens for the two lines of the illumination optical system and the observation optical system. The respective distal end of the optical system lumen 5 is hermetically closed off by a translucent cover 7. That prevents contamination of the optical system 6 at the target location. The remaining part of the optical system 6 is protected from contamination by the enclosure formed by the catheter probe 1. The optical system 6 can be displaced forwardly in the optical system passage 4 for example by means of an optical system slider fitted on to the optical system exit 11, as far as the translucent cover 5 which can be in the form of a glass plate or disc.

The light guide fibre bundle of the optical system 6, which projects beyond the proximal end of the catheter probe 1 and the lumen exit 37, is guided in the axial direction in a flexible tube 2. The tube 2 forms a protection for the optical system in relation to external influences and in addition the tube 2 is of an elastically resilient nature in its longitudinal direction. At its front (distal) end the tube 2 has a coupling portion which with the proximal lumen exit 37 forms a releasable fixing device 46, for example a Luer lock. The rear (proximal) end 8 of the tube is also equipped with a coupling element which can be releasably connected to a connecting portion 10, forming a releasable fixing location 3. The releasable fixing location 3 can be in the form of a Luer lock connection. It is also possible to provide a bayonet connection. The connecting portion 10 is disposed at the proximal end of the light guide fibre bundle of the optical system 6.

When the distal end of the tube 2 is connected to the lumen exit 37 and the proximal end 8 of the tube is connected to the connecting portion 10, the tube 2 is stretched so that a prestressing is applied to the optical system 6 in the longitudinal direction thereof. That prestressing provides that the distal end 4 of the optical system is pressed against the cover 7 at the distal end of the optical system lumen. That prestressing guarantees that, even when the distal portion 24 of the probe is bent away, the distal end 4 of the optical system is always pressed against the translucent cover 7 so as to guarantee satisfactory observation of the target location. The resilient prestressing force afforded by the tube 2 guarantees automatic forward displacement of the optical system when the distal end 20 of the probe is bent. When the end 20 of the probe is brought back into its straight position, the optical system 6 is pushed back against the prestressing force. That guarantees that the optical system 6 always bears with its distal end against the cover 7, under a given pressing force.

The proximal end of the illumination optical system bundle can be connected by way of the connecting portion 10 to an illumination device, for example an emergency illumination system. For that purpose the attachment portion 10 has a corresponding adaptor device 44. The proximal end of the observation optical system bundle of the optical system 6 can be connected to an observation device. The observation device includes an ocular which can be connected to the observation optical system bundle of the optical system 6 by way of the connecting portion 10 by means of a suitable adaptor device 45, for example a bayonet fixing. The observation device can also be in the form of a camera/monitor system.

As can be seen from FIG. 4 the catheter probe 1 can have a balloon 17 at a given spacing from the distal end 20 of the probe. To expand the balloon 17, a liquid or gaseous dilation medium is fed to the balloon 17 by way of the balloon lumen 18. In that case the balloon 17 can be expanded in diameter by approximately 1.0 to 1.5 mm with respect to the probe diameter. For example the outside diameter of the catheter probe can be 1.8 mm, in which case the balloon can be expanded to about 3.0 mm. The balloon 17 can be of a length of about 20 mm. The distance of the balloon 17 to the distal end of the probe can be about 25 mm to 35 mm, in particular 30 mm.

A guide wire 11 can be guided through a guide wire lumen 17 which is open at the distal end 20 of the probe. In that way it is possible for the distal region of the catheter probe 1 and in particular the region of the distal portion 24 of the probe, which is to be bent over, and the balloon 17, to be introduced into the body of a patient by means of the guide wire 11. The guide wire lumen 19 terminates behind the balloon 17, as viewed from the distal end 20 of the probe, and issues outwardly by way of an exit opening 21 in the catheter wall 22. The exit opening can be predetermined in the proximity of the proximal end of the probe. The distance from the distal end 20 of the probe to the exit opening 21 can be for example 230 mm.

As the catheter probe 1 and the proximal probe attachment portion 33 with the associated lumen exits 34 to 37 can be produced in the form of a disposable component, for example using injection moulding, only the respective surgical instrument used still remains for the decontamination treatment. In the case of an integrated or incorporated instrument the decontamination treatment is also eliminated for same. The handle 12 is of such a design configuration that it can be used with various different catheter probes which have a control element in the manner of the control element 13.

A catheter probe 1 of the cross-sectional shape shown in FIG. 3 can be for example of an outside diameter of 1.8 mm+0.05 mm. The inside diameter of the optical system passage 5 can be for example 0.85+0.02. The diameter for the balloon passage 18 can be for example 0.22+0.02 mm. The inside diameter of the guide wire lumen 19 can be for example 0.47+0.02 mm. The inside diameter of the working lumen 29 which can also be used as a flushing lumen can be for example 0.6+0.02 mm. The inside diameter of the control lumen 25 can be for example 0.47+0.02 mm. The specified diameter dimensions can vary in relation to catheter probes for different purposes of use. However the handle, the optical system and the ocular can be used in a unitary manner for the different catheter probes. With varying lengths in respect of the catheter probe 1, those lengths can be compensated by means of different tubes 2 of corresponding lengthwise dimensions so that, even for catheter probes of differing lengths, it is possible to use a single optical system 6 with the associated connecting portion.

The described endoscope can be used for example for coronary blood vessel endoscopy, in which case the catheter probe 1 can be equipped with the balloon 17 in its distal probe region.

Furthermore the handle 12 can be employed with different catheter probes for use in cholangioscopy and mechanical lithotripsy, in particular percutaneous mechanical lithotripsy and other endoscopic interventions.

The invention claimed is:

1. An endoscope comprising a flexible catheter probe having a plurality of lumens, a handle provided at a proximal end of the flexible catheter probe, an optical system provided removably in at least one optical system lumen of the flexible catheter probe, at least one working lumen for a surgical instrument and a control element which is fixed to a distal end of the flexible catheter probe or in proximity thereof for bending the distal end of the flexible catheter probe and is guided movably in an axial direction of the flexible catheter probe, wherein:
the optical system which projects beyond the proximal end of the flexible catheter probe is guided movably in a flexible tube which is elastically resilient in a longitudinal direction thereof to prestress the optical system toward the distal end of the flexible catheter probe and a proximal end of the flexible tube is fixedly connected at a fixing location to the optical system projecting beyond the proximal end of the flexible catheter probe and its distal end is releasably connected to a proximal end of the optical system lumen of the flexible catheter probe;

a distal end of the optical system is pressed by the tube against a translucent cover which closes the distal end of the optical system lumen;

a rotary bearing is provided on the handle;

at its proximal end, the flexible catheter probe is non-rotatably connected by a releasable fixing device to a manually actuatable rotary portion which is mounted rotatably to the handle by the rotary bearing, and wherein the flexible catheter probe rotates 360° with respect to the handle;

the control element is displaceably guided in the rotary bearing;

a proximal end of the control element is releasably connected to a slider mounted to the handle so as to permit movement of the control element in the axial direction; and the flexible catheter probe is a disposable component.

2. An endoscope according to claim 1, wherein the fixing location is provided at the proximal end of the flexible tube.

3. An endoscope according to claim 1, wherein provided at the proximal end of the optical system is a connecting portion which is connectable to an illumination device and/or to an ocular.

4. An endoscope according to claim 3, wherein the fixing location is provided at the connecting portion.

5. An endoscope according to claim 1, wherein the flexible tube is arranged outside the handle.

6. An endoscope according to claim 1, wherein the control element is passed through the releasable fixing device.

7. An endoscope according to claim 6, wherein the control element is arranged in a flexible support tube which is arranged in a control lumen of the flexible catheter probe and terminates at a given spacing from the distal end of the flexible catheter probe, wherein the given spacing corresponds approximately to a length of a distal portion of the flexible catheter probe, which is to be bent over by the control element.

8. An endoscope according to claim 6, wherein the control element is fixed to the distal end of the flexible catheter probe by a shrink tube or by an adhesive.

9. An endoscope according to claim 8, wherein a support tube is fixed to the flexible catheter probe in the axial direction and a remaining portion of the support tube is supported movably with respect to an inside wall of a control lumen.

10. An endoscope according to claim 8, wherein a support tube is fixed to the flexible catheter probe at a distal end of the support tube or in proximity thereof.

11. An endoscope according to claim 1, wherein the proximal end of the control element is passed through the releasable fixing device.

12. An endoscope according to claim 1, wherein the flexible catheter probe has a balloon to which a dilation medium can be fed by way of a balloon lumen in the flexible catheter probe.

13. An endoscope according to claim 12, wherein a guide wire can be guided through a guide wire lumen which extends from the distal end of the flexible catheter probe to an exit opening in the flexible catheter probe, the exit opening being behind the balloon.

14. An endoscope according to claim 1, wherein the surgical instrument is removable from the at least one working lumen or is incorporated or integrated into the flexible catheter probe.

15. An endoscope according to claim 1, wherein the flexible catheter probe is an injection molded component or an extruded component.

* * * * *